(12) United States Patent
Desai et al.

(10) Patent No.: US 10,385,017 B2
(45) Date of Patent: Aug. 20, 2019

(54) PYRROLE COMPOUND, COMPOSITIONS AND PROCESS FOR PREPARATION THEREOF

(71) Applicant: Cadila Healthcare Ltd., Ahmedabad, Gujarat (IN)

(72) Inventors: Sanjay Jagdish Desai, Gujarat (IN); Ramesh Chandra Singh, Gujarat (IN); Daya Ram Pal, Gujarat (IN); Dharmendra Arvindbhai Darji, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 0 days.

(21) Appl. No.: 15/748,316

(22) PCT Filed: Oct. 13, 2016

(86) PCT No.: PCT/IB2016/056120
§ 371 (c)(1),
(2) Date: Jan. 29, 2018

(87) PCT Pub. No.: WO2017/064635
PCT Pub. Date: Apr. 20, 2017

(65) Prior Publication Data
US 2018/0265466 A1  Sep. 20, 2018

(30) Foreign Application Priority Data

Oct. 14, 2015 (IN) .......................... 3901/MUM/2015

(51) Int. Cl.
*C07D 207/333* (2006.01)
*A61K 31/40* (2006.01)
*A61K 31/4025* (2006.01)

(52) U.S. Cl.
CPC .......... *C07D 207/333* (2013.01); *A61K 31/40* (2013.01); *A61K 31/4025* (2013.01)

(58) Field of Classification Search
CPC . C07D 207/333; A61K 31/40; A61K 31/4025
USPC ....................................................... 514/422
See application file for complete search history.

(56) References Cited

U.S. PATENT DOCUMENTS

| | | | |
|---|---|---|---|
| 4,231,938 A | 11/1980 | Monaghan et al. |
| 4,346,227 A | 8/1982 | Terahara et al. |
| 4,444,784 A | 4/1984 | Hoffman et al. |
| 5,273,995 A | 12/1993 | Roth |
| 5,354,772 A | 10/1994 | Kathawala |
| 6,166,063 A | 12/2000 | Villhauer |
| 6,395,767 B2 | 5/2002 | Robl et al. |
| 6,699,871 B2 | 3/2004 | Edmondson et al. |
| 6,987,123 B2 | 1/2006 | Lohray et al. |
| 7,041,837 B2 | 5/2006 | Lohray et al. |
| 7,323,491 B2 | 1/2008 | Lohray et al. |
| 7,407,955 B2 | 8/2008 | Himmelsbach et al. |
| 8,110,598 B2 | 2/2012 | Lohray et al. |
| 8,212,057 B2 | 7/2012 | Lohray et al. |
| 8,558,009 B2 | 10/2013 | Lohray et al. |
| 8,772,342 B2 | 7/2014 | Darteil et al. |
| 9,610,277 B2 | 4/2017 | Patel et al. |
| 9,656,954 B2 | 5/2017 | Jain et al. |
| 9,783,495 B2 | 10/2017 | Pandey et al. |
| 9,814,697 B2 | 11/2017 | Patel et al. |
| 2003/0199498 A1 | 10/2003 | Lohray et al. |
| 2003/0236254 A1 | 12/2003 | Lohray et al. |
| 2007/0238776 A1 | 10/2007 | Lohray et al. |
| 2009/0196923 A1 | 8/2009 | Mandal et al. |
| 2011/0275669 A1 | 11/2011 | Lohray et al. |
| 2012/0121729 A1 | 5/2012 | Paterson et al. |
| 2013/0338209 A1 | 12/2013 | Gambhire et al. |
| 2016/0068484 A1 | 3/2016 | Jain et al. |
| 2016/0107989 A1 | 4/2016 | Dwivedi et al. |
| 2016/0136131 A1 | 5/2016 | Patel et al. |
| 2016/0166539 A1 | 6/2016 | Patel et al. |
| 2016/0194280 A1 | 7/2016 | Dwivedi et al. |
| 2016/0207884 A1 | 7/2016 | Dwivedi et al. |
| 2017/0087127 A1 | 3/2017 | Patel et al. |
| 2017/0088514 A1 | 3/2017 | Gambhire et al. |
| 2017/0144968 A1 | 5/2017 | Dwivedi et al. |
| 2017/0266158 A1 | 9/2017 | Patel et al. |

FOREIGN PATENT DOCUMENTS

| | | |
|---|---|---|
| EP | 1586571 A1 | 10/2005 |
| EP | 1725234 A1 | 11/2006 |
| IN | 1910/MUM/2013 | 12/2014 |
| WO | 1991/19702 A1 | 12/1991 |
| WO | 1994/01420 A1 | 1/1994 |
| WO | 1994/13650 A1 | 6/1994 |
| WO | 1995/03038 A1 | 2/1995 |

(Continued)

OTHER PUBLICATIONS

Acdisol Product Overview (year 2005).
Angulo, P. "GI Epidemiology: nonalcoholic fatty liver disease," Aliment. Pharmacol. Ther. (2007) vol. 25, No. 8, pp. 883-889.
Anonymous "IND Minutes draft 19 07 12" Retrieved on Oct. 15, 2013 from the Internet from URL: http://www.docstoc.com/docs/145152750/IND-Minutes-draft-19-07-12 (1 page).
Anonymous "LipaglynTM Discovery, Development & Preclinical Studies" Retrieved on Oct. 15, 2013 from the Internet from URL: http://webcache.googleusercontent.com/search?q=cacheRGrhinY0HM3sJ:lipaglyn.com/downloads/Lipaglyn_Preclinical_Studies.ppsx (25 pages).
Anonymous International Nonproprietary Names for Pharmaceutical Substances (INN); Jan. 1, 2012; Retrieved from the internet: URL: http://www.who.int/medicines/publications/druginformation/issues/PL_108.pdf; Retrieved on Oct. 15, 2013; pp. 401-471.

(Continued)

*Primary Examiner* — Kristin A Vajda
(74) *Attorney, Agent, or Firm* — Goodwin Procter LLP

(57) ABSTRACT

The present invention relates to compositions comprising saroglitazar magnesium wherein the saroglitazar magnesium has a purity of greater than or equal to 99% by weight, and dimer compound of Formula (IV) present in an amount relative to saroglitazar magnesium less than about 0.3% by weight by area percentage of HPLC. The present invention also related to the process for the preparation thereof and pharmaceutical compositions comprising the same.

20 Claims, 1 Drawing Sheet

(56) References Cited

FOREIGN PATENT DOCUMENTS

| | | |
|---|---|---|
| WO | 1995/17394 A1 | 6/1995 |
| WO | 1996/04260 A1 | 2/1996 |
| WO | 1996/04261 A1 | 2/1996 |
| WO | 1996/33998 A1 | 10/1996 |
| WO | 1997/25042 A1 | 7/1997 |
| WO | 1997/36579 A1 | 10/1997 |
| WO | 1998/028534 A1 | 7/1998 |
| WO | 1999/08501 A2 | 2/1999 |
| WO | 1999/16758 A1 | 4/1999 |
| WO | 1999/19313 A1 | 4/1999 |
| WO | 1999/20614 A1 | 4/1999 |
| WO | 2000/23417 A1 | 4/2000 |
| WO | 2000/23445 A1 | 4/2000 |
| WO | 2000/23451 A1 | 4/2000 |
| WO | 2001/53257 A2 | 7/2001 |
| WO | 2002/24625 A2 | 3/2002 |
| WO | 2003/009841 A1 | 2/2003 |
| WO | 2005/031335 A1 | 4/2005 |
| WO | 2011/079257 A2 | 6/2011 |
| WO | 2011/123401 A1 | 10/2011 |
| WO | 2012/104869 A1 | 8/2012 |
| WO | 2012/162129 A1 | 11/2012 |
| WO | 2013/106358 A1 | 7/2013 |
| WO | 2013/163508 A1 | 10/2013 |
| WO | 2013/169648 A1 | 11/2013 |
| WO | 2014/019919 A1 | 2/2014 |
| WO | 2014/174524 A1 | 10/2014 |
| WO | 2014/195967 A2 | 12/2014 |
| WO | 2015/001573 A1 | 1/2015 |
| WO | 2015/011730 A1 | 1/2015 |
| WO | 2015/029066 A1 | 3/2015 |
| WO | 2015/033357 A2 | 3/2015 |

OTHER PUBLICATIONS

Ansel et al. "Pharmaceutical Dosage Forms and Drug Delivery Systems, Seventh Edition" 1999, pp. 88-92.

Arnett et al., "Solvent Effects in Organic Chemistry. V. Molecules, Ions, and Transition States in Aqueous Ethanol", J. Am. Chem. Soc., 1965, 87(7), pp. 1541-1553.

Augustyns, K. et al. "Inhibitors of proline-specific dipeptidyl peptidases: DPP IV inhibitors as a novel approach for the treatment of Type 2 diabetes," Expert Opin. Ther. Patents, (2005) vol. 15, No. 10, pp. 1387-1407.

Barb et al. (2016) "Pharmacological management of nonalcoholic fatty liver disease" Metabolism Clinical and Experimental 65:1183-1195.

Berge et al., "Phamaceutical Salts", Journal of Pharmaceutical Sciences, 1977, vol. 66, No. 1, pp. 1-19.

Berger et al. (2005) "PPARs: Therapeutic targets for metabolic disease Trends in Pharmacological Sciences" 26(5): 244-251.

Bharate, S. et al. "interactions and incompatibilities of pharmaceutical excipients with active pharmaceutical ingredients: a comprehensive review." J. Excipient and Food Chem. (2010) vol. 1, No. 3, pp. 3-26.

Boettcher, E. et al. "Meta-analysis: pioglitazone improves liver histology and fibrosis in patients with non-alcoholic steatohepatitis," Aliment. Pharmacol. Ther. (2012) vol. 35, No. 1, pp. 66-75, (Abstract Only).

Boulet, L-P. "influence of Comorbid Conditions on Asthma" European Respiratory Journal (2009) vol. 33, pp. 897-906.

Brenna, E. et al. "Enzyme-mediated synthesis of EEHP and EMHP, useful pharmaceutical intermediates of PPAR agonists" Tetrahedron: Asymmetry (2009) vol. 20, pp. 2594-2599.

Bugianesi, E. et al. "Insulin Resistance: A Metabolic Pathway to Chronic Liver Disease," Hepatology (2005) vol. 42, No. 5, pp. 987-1000.

Cairns, D. (editor) "Essentials of Pharmaceutical Chemistry, Fourth Edition" 2012, p. 14.

Chait, A. et al., "Chyloi-nicronemia Syndrome," Adv, Intern. Med., (1992), vol. 37, pp. 249-273; (Abstract).

Chatila, W. M. et al. "Comorbidities in Chronic Obstructive Pulmonary Disease" Proc. Am, Thorac. Soc. (2008) vol. 5, pp. 549-555.

Chaumeil, J.C., "Micronization: A Method of Improving the Bioavailability of Poorly Soluble Drugs", Methods and Findings in Experimental and Clinical Phamacology, Apr. 1998, vol. 20, No. 3, pp. 211-215.

Choi, "Amorphous ultrafine particle preparation for improvement of bioavailability of insoluble drugs: grinding characteristics of fine grinding mills", international Journal of Mineral Processing, vol. 74 Supplement 1, Dec. 10, 2004, pp. S165-S172.

Chou et al, (2013) "Metreleptin: First Global Approval" Drugs 73:989-997.

Deeg et al. (2007) "Pioglitazone and Rosiglitazone Have Different Effects on Serum Lipoprotein Particle Concentrations and Sizes in Patients With Type 2 Diabetes and Dyslipidemia" Diabetes Care 30(10):2458-2464.

Demuth, H.-U. et al. "Type 2 diabetes—Therapy with dipeptidyl peptidase IV inhibitors," Biochim. Biophys. Acta, 1751 (2005) pp. 33-44.

Fan, W. and Evans, R. "PPARs and ERRs: molecular mediators of mitochondrial metabolism" Curr. Opin. Cell Bio. (2015) vol. 33, pp. 49-54.

FDA News Release—FDA Approves Egrifta to treat Lipodystrophy in HIV Patients; downloaded from www.fda.gov/NewsEvents/Newsroom/PressAnnouncements/ucm233516.htm on Sep. 7, 2016 (2 pages).

Fredrickson, D.S., et al., "A system for Phenotyping Hyper Lipoproteinernia," Circulation, Mar. 1965, 31, pp. 321-327.

Friedman, M. et al., "The Mechanism Responsible for the Hypercholesteremia Induced by Triton WR-1339", J. Exp. Med., 1953, vol. 97, No. 1, pp. 117-130.

Gennaro et al. "Remington's Pharmaceutical Sciences, 19th Edition" (1995) Mack Publishing, pp. 1380-1383.

Giri et al. "Efficacy of Saroglitazar, a Novel PPAR Agonist in a Mouse Model of Non-Alcoholic Steatohepatitis" Poster No. 2011, Keystone Symposia Conference, Mar. 22-27, 2015 at Whistler, British Colombia; Canada.

Guo, Z. et al., "Free fatty acid turnover measured using uitraiow doses of [U-130] palmitate," Journal of Lipid Research, 1997, vol. 38, pp. 1888-1895.

Hadigan, C. et al. "Metabolic Effects of Rosiglitazone in HIV Lipodystrophy: A Randomized, Controlled Trial," Ann. Internal Med. (2004) vol. 140, No. 10, pp. 786-794. (Abstract Only).

Herrine, S. K. "Nonalcoholic Steatohepatitis (NASH)" Merck Manual (Revised May 2016) Retrieved from http://www.merckmanuals.com/professional/hepatic-and-biliary-disorders/approach-to-the-patient-with-liver-disease/nonalcoholic-steatohepatitis-nash. (3 pages).

IND Committee: "Minutes of IND Committee Meeting Held on Jul. 19, 2012" Retrieved on Oct. 15, 2013 from the Internet from URL: http://www.docstoc.com/docs/145152750/IND-Minutes-draft-19-07-12 (2 pages).

International Preliminary Report on Patentability dated Aug. 6, 2013 for International Application No. PCT/IN2012/000069 (5 pages).

International Preliminary Report on Patentability dated Dec. 10, 2015 for International Patent Application No. PCT/IN2014/000367 (10 pages).

International Preliminary Report on Patentability dated Jul. 9, 2015 for international Application No. PCT/IN2013/000391 (9 pages).

International Preliminary Report on Patentability dated Mar. 1, 2016 for Application No. PCT/IN2014/000551 (7 pages).

International Preliminary Report on Patentability dated Mar. 8, 2016 for International Patent Application No. PCT/IN2014/000584 (10 pages).

International Preliminary Report on Patentability dated Oct. 6, 2015 for International Patent Application No. PCT/IN2014/000445 (7 pages).

International Preliminary Report on Patentability dated Oct. 9, 2015 for International Application No. PCT/IN2014/000489 (7 pages).

International Search Report and Written Opinion dated Dec. 19, 2014 for Application No. PCT/IN2014/000551 (11 pages).

(56) References Cited

OTHER PUBLICATIONS

International Search Report and Written Opinion dated Dec. 23, 2014 for International Patent Application No. PCT/IN2014/000445 (10 pages).
International Search Report and Written Opinion dated Feb. 2, 2015 for International Patent Application No. PCT/IN2014/000367 (10 pages).
International Search Report and Written Opinion dated Mar. 23, 2015 for Application No. PCT/IN2014/000584 (12 pages).
International Search Report and Written Opinion dated Nov. 20, 2013 for International Application No. PCT/IN2013/000391 (13 pages).
International Search Report and Written Opinion dated Nov. 20, 2014 for International Application No. PCT/IN2014/000489 (10 pages).
International Search Report dated May 9, 2012 for International Application No. PCT/IN2012/000069 (3 pages).
Jackson, K. "No Benefit from Ezetimibe in NASH" in Medpage Today (Jun. 2015).
Jain et al. "Saroglitazar Shows Therapeutic Benefits in Mouse Model of Non-alcoholic Fatty Liver Disease (NAFLD) and Non-alcoholic Steatohepatitis (NASH)" Poster No. 1957-P, 75th Scientific Session—ADA, Jun. 5-9, 2015, Boston, MA, USA.
Jani, R. H. et al. "Pharmacokinetics, Safety, and Tolerability of Saroglitazar (ZYH1), a Predominantly PPARα Agonist with Moderate PPARg Agonist Activity in Healthy Human Subjects" Clin. Drug Investig. (2013) vol. 33, pp. 809-816.
Jani, R. H. et al. "A Multicenter, Prospective, Randomized, Double-Blind Study to Evaluate the Safety and Efficacy of Saroglitazar 2 and 4 mg Compared with Placebo in Type 2 Diabetes Mellitus Patients Having Hypertriglyceridemia Not Controlled with Atorvastatin Therapy (Press VI)," Diabetes Technology & Therapeutics, (2014) vol. 16, No. 2, pp. 63-71.
Jani, R. H. et al. "A Prospective Randomized, Double Blind, Placebo Controlled Study to Evaluate the Safety, Tolerability and Pharmacokinetics of ZYH1 Following Once a Day (OD) Oral Administrations up to 10 Days in Healthy Volunteers," Diabetes (2009) vol. 58, No. Suppl. 1, p. A569.
LaBrecque, D. et al. "World Gastroenterology Organisation, Global Guidelines: Nonalcoholic Fatty Liver disease and Nonalcoholic Steatohepatitis (long version)" World Gastroenterology Organisation (2012) 29 pages.
Lemoine, M. et al. "Steatohepatitis (fatty liver) Is Associated With Increased Hepatic Expression of SREBP-1 in HIV-Infected Patients With Antiretroviral Therapy-Linked Lipodystrophy," Abstract from 55th Annual Meeting of the American Association for the Study of Liver Diseases, Oct. 29 to Nov. 2, 2004; Printed from http://www.natap.org/2004/AASLD/aasld_10.htm. (8 pages).
Lieberman, et al. "Pharmaceutical Dosage Forms: Tablets, vol. 1, 2nd Edition" (1989) Marcel Dekker Inc., pp. 111-114.
Macallan, D. C. et al. "Treatment of Altered Body Composition in HIV Associated Lipodystrophy: Comparison of Rosiglitazone, Pravastatin, and Recombinant Human Growth Hormone," HIV Clinical Trials, (2008) vol. 9, Issue 4, pp. 254-268. (Abstract Only).
Mastracchio, A., "Phase-transfer catalysis", MacMillan Lab Group Meeting (power point presentation) Apr. 20, 2008, 1-53.
Ooi et al., "Recent advances in asymmetric phase-transfer catalysis", Angew. Chem. Int. Ed. Engl., 2007, 46, 4222-4266.
Otway, S. et al., "The Use of a Non-Ionic Detergent (Triton WR1339) to Determine Rates of Triglyceride entry into the Circulation of the Rat under Different Physiological Conditions", J. Physiol., 1967, vol. 190, No. 2, pp. 321-332.
Package Insert for ACTOS (pioglitazone) tablets for oral use (2013).
Package Insert for AVANDIA (rosiglitazone maleate) Tablets (2008).
Pai, V. et al. "A Multicenter, Prospective, Randomized, Double-blind Study to Evaluate the Safety and Efficacy of Sarogiltazar 2 and 4 mg Compared to Pioglitazone 45 mg in Diabetic Dyslipidernia (Press V)." J. Diabetes Sci. Technol. (2014) vol. 8, No. 1, pp. 132-141.
Palomer et al. (2016) "PPARb/d and lipid metabolism in the heart" Biochemica et Biophysica Acta 1861:1569-1578.
Pharmatrans Sanaq AG "LubriSanaq®—Sodium Stearyl Fumarate" Dated Feb. 5, 2008. Retrieved on Jan. 23, 2017 from the Internet at URL: http:www.pnarmaceutical-tecnnology.com/contractors/excipients/pharmatrans-sanaq/press9.html. (2 pages).
Prescribing Information for Zetia® (ezetirnibe; year 2012).
Rakoski, M. et al. "Meta-analysis: Insulin Sensitizers for the Treatment of Non-alcoholic Steatohepatitis" Ailment, Pharmacol. Ther. (2010) vol. 32, pp. 1211-1221.
Ramirez; T. et al. "Structural Correlates of PPAR Agonist Rescue of Experimental Chronic Alcohol-Induced Steatohepatitis," J. Olin. Exper. Pathology (2012) vol. 2, No. 4, pp. 114.
Response to Written Opinion filed on May 21, 2015 for International Application No. PCT/IN2014/000489 (6 pages).
Santamarina-Fojo, S., "The Familial Chylomicronernia Syndrome", Lipid Disorders, 1998, 27(2): pp. 551-567.
Scanu, A. et al., "Triton Hyperlipemia in Dogs: In Vitro Effects of Tire Detergent on Serum Lipoproteins and Chylomicron," JEM, 1961, vol. 113, No. 4, pp. 735-757.
Seo, Y, S. et al. "PPAR agonists treatment is effective in a nonalcoholic fatty liver disease animal model by modulating fatty-acid metabolic enzymes" J. Gatroenterology Hepatology (2008) vol. 23, No. 1, pp. 102-109.
Sodium Stearyl Furnarate, obtained on Jun. 23, 2015. Retrieved from the Internet: <URL: https://www.medicinescomplete.com/me/excipients/current/ . . . >, 4 pages.
Sosale, A., et al., "Saroglitazar for the Treatment of Hypertriglyceridemia in Patients with Type 2 Diabetes: Current Evidence," Diebetes, Metabolic Syndrome and Obesity: Targets and Therapy, vol. 8; Jan. 1, 2015, pp. 189-196.
Tungsiripat, M. et al. "Rosiglitazone improves lipoatrophy in patients receiving thymidine-sparing regimens," AIDS, (2010) vol. 24, pp. 1291-1298.
USPTO Trademark Database Entry for AEROSIL, 1966.
van Wijk, J. P. H. et al. "Comparison of Rosiglitazone and Metformin for Treating HIV Lipodystrophy: A Randomized Trial," Ann. Internal Med. (2005) vol. 143, No. 5, pp. 337-346.
Vatner, D.F. et al., "Insulin-independent regulation of hepatic triglyceride synthesis by fatty acids", PNAS, vol. 112, No. 4, pp. 1143-1148, 2015.
Written Opinion of the International Searching Authority dated May 9, 2012 for International Application No. PCT/IN2012/000069 (4 pages).
Yessoufou et al. (2010) "Multifaceted roles of peroxisome proliferator-activated receptors (PPARs) at the cellular and whole organism levels" Swiss Medical Weekly 140:w13071.

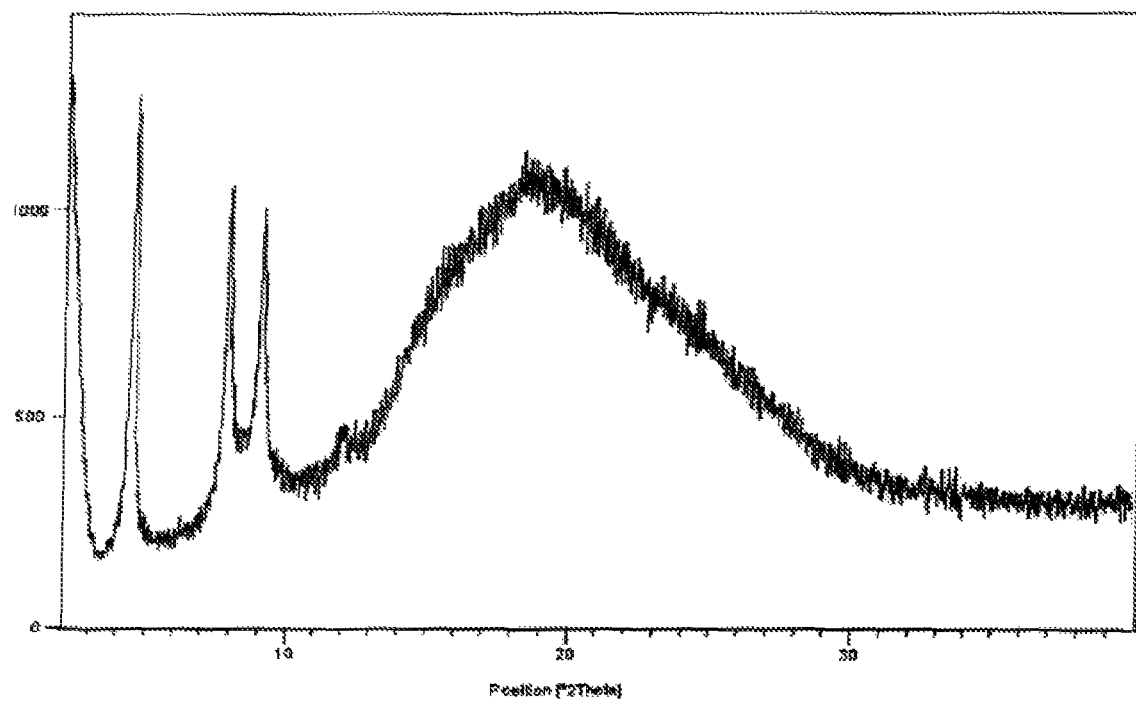

PYRROLE COMPOUND, COMPOSITIONS AND PROCESS FOR PREPARATION THEREOF

CROSS-REFERENCE TO RELATED APPLICATIONS

This application is the national stage of International (PCT) Patent Application serial number PCT/IB2016/056120, filed Oct. 13, 2016, which claims the benefit of and priority to Indian Patent Application serial number 3901/MUM/2015, filed Oct. 14, 2015; the contents of International (PCT) Patent Application serial number PCT/IB2016/056120 are hereby incorporated by reference in their entirety.

FIELD OF THE INVENTION

The present invention relates to pyrrole compound, compositions and process for the preparation thereof. In particular, the invention relates to saroglitazar magnesium, compositions and process for the preparation of saroglitazar magnesium.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Pyrrole derivative of present invention is chemically 2-ethoxy-3-(4-(2-(2-methyl-5-(4-(methylthio)phenyl)-1H-pyrrol-1-yl)ethoxy)phenyl)propanoate, which may be optically active or racemic and its pharmaceutically acceptable salts, hydrates, solvates, polymorphs or intermediates thereof. The INN name for pyrrole derivative is Saroglitazar® which is marketed as its magnesium salt of Formula (I), having below chemical structure.

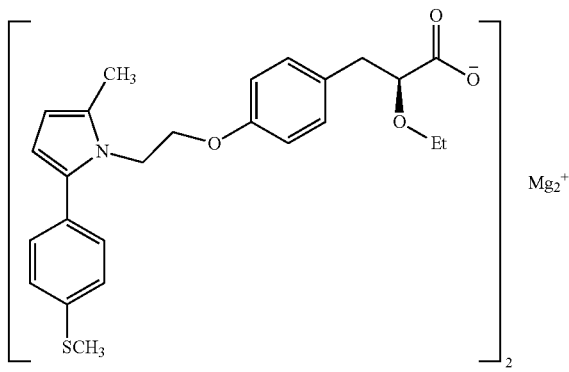

(I)

The compound of Formula (I) lower or modulate triglyceride levels and/or cholesterol levels and/or lower density lipoproteins (LDL) and raise HDL plasma levels and hence are useful in combating different medical conditions, where such lowering (and raising) is beneficial. Thus, it could be used in the treatment and/or prophylaxis of obesity, hyperlipidemia, hypercholesteremia, hypertension, atherosclerotic disease events, vascular restenosis, diabetes and many other related conditions. The compound of Formula (I) are useful to prevent or reduce the risk of developing atherosclerosis, which leads to diseases and conditions selected from arteriosclerotic cardiovascular diseases, stroke, coronary heart diseases, cerebrovascular diseases, peripheral vessel diseases and related disorders.

U.S. Pat. No. 6,987,123 B2 discloses novel heterocyclic compounds, their preparation, pharmaceutical compositions containing them and their use in medicine. The patent discloses different pathways for the synthesis of pyrrole derivatives.

U.S. Pat. Nos. 7,041,837 B2, 7,323,491 B2, 8,110,598 B2, 8,212,057 B2 disclose different pyrrole derivatives and their intermediates.

International (PCT) Publication No. WO 2012/104869 provides the use of compound of Formula (I) for the treatment of lipodystrophy.

International (PCT) Publication No. WO 2014/195967 discloses process for the preparation of saroglitazar and its pharmaceutically acceptable salts thereof.

International (PCT) Publication No. WO 2015/029066 discloses polymorphic form of saroglitazar free acid and its pharmaceutically acceptable salts thereof.

International (PCT) Publication No. WO 2015/033357 discloses an improved process for the preparation of saroglitazar magnesium.

The different physical properties exhibited by polymorphs affect important pharmaceutical parameters selected from storage, stability, compressibility, density and dissolution rates (important in determining bioavailability). Stability differences may result from changes in chemical reactivity (e.g., differential hydrolysis or oxidation, such that a dosage form discolors more rapidly when comprised of one polymorph than when comprised of another polymorph), mechanical changes (e.g., tablets crumble on storage as a kinetically favored crystalline form converts to thermodynamically more stable crystalline form) or both (e.g., tablets of one polymorph are more susceptible to breakdown at high humidity). Solubility differences between polymorphs may, in extreme situations, result in transitions to crystalline forms that lack potency or are toxic. In addition, the physical properties of the crystalline form to that of an amorphous form may be important in pharmaceutical processing. For example, an amorphous form may provide better bioavailability than the crystalline form.

Therefore, it may be desirable to have an amorphous form of drugs with high purity to meet the regulatory requirements and also highly reproducible processes for their preparation.

In view of the above, it is therefore, desirable to provide an efficient, more economical, less hazardous and eco-friendly process for the preparation of saroglitazar magnesium having high purity. However, the present invention provides a process for the preparation of saroglitazar magnesium and compositions thereof suitable for development of finished formulations having high purity.

SUMMARY OF THE INVENTION

The present invention features saroglitazar magnesium, compositions and process for its preparation. The compositions of saroglitazar magnesium are useful in the treatment and conditions, including but not limited to prophylaxis of obesity, hyperlipidemia, hypercholesteremia, hypertension, atherosclerotic disease events, vascular restenosis, diabetes and to prevent or reduce the risk of developing atherosclerosis, which leads to diseases and conditions selected from arteriosclerotic cardiovascular diseases, stroke, coronary heart diseases, cerebrovascular diseases, peripheral vessel diseases and related disorders.

In one general aspect there is provided a composition comprising saroglitazar magnesium and a dimer compound of Formula (IV).

In one embodiment, the dimer compound comprises the structure of Formula (IV),

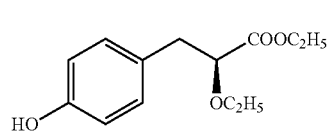

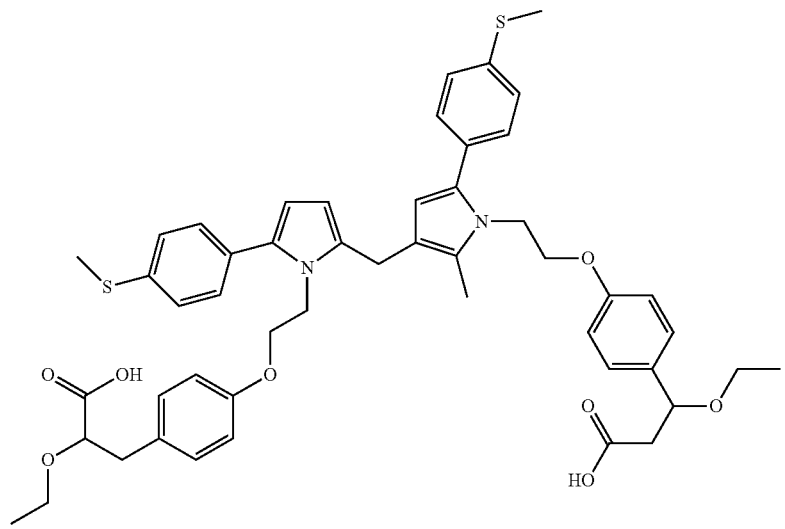 [SMILES: CCOC(Cc1ccc(OCCn2c(Cc3cc(-c4ccc(SC)cc4)n(CCOc4ccc(C(CC(=O)O)OCC)cc4)c3C)ccc2-c2ccc(SC)cc2)cc1)C(=O)O]

In another general aspect there is provided a composition comprising saroglitazar magnesium and a sulfoxide compound of Formula (V).

In second embodiment, the sulfoxide compound comprises the structure of Formula (V),

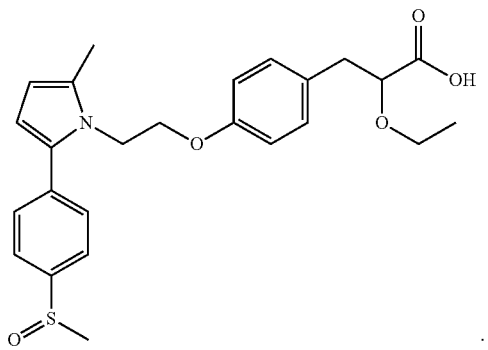 [SMILES: CCOC(Cc1ccc(OCCn2c(C)ccc2-c2ccc(S(C)=O)cc2)cc1)C(=O)O]

In another general aspect there is provided a pharmaceutical composition of saroglitazar magnesium of the present invention.

In another general aspect there is provided a process for the preparation of substantially pure saroglitazar magnesium, the process comprising:

(a) reacting a hydroxy compound (A) with a mesylate compound (A1) in one or more solvents in the presence of a base to obtain an alkoxy ester compound of Formula (II);

-continued

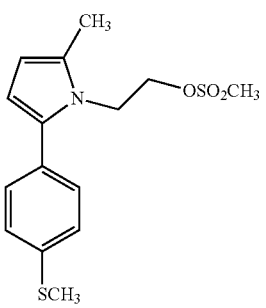

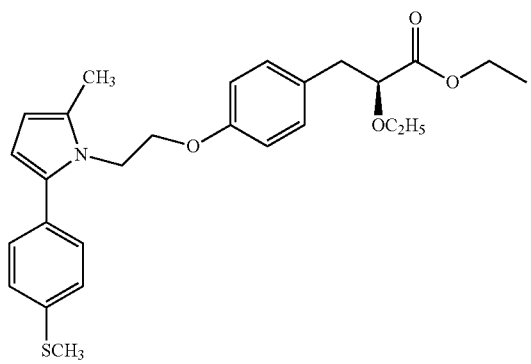

(b) hydrolyzing the alkoxy ester compound of Formula (II) with a base in one or more solvents at a lower temperature to obtain a reaction mixture;
(c) optionally, washing the reaction mixture with one or more solvents to obtain an aqueous layer;

(d) treating the aqueous layer with one or more solvents and adjusting the pH 2.0 to 6.0;
(e) extracting the aqueous layer with one or more solvents to obtain an organic layer;
(f) treating the organic layer with S-(−)-α-methylbenzyl amine to obtain saroglitazar S-(−)-α-methylbenzyl amine (SMBA) salt of Formula (III);

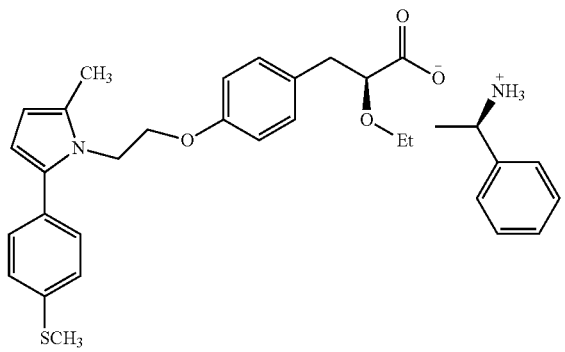

(g) purifying the saroglitazar SMBA salt with one or more solvents to obtain pure saroglitazar SMBA salt; and
(h) treating the pure saroglitazar SMBA salt with magnesium source to obtain the substantially pure saroglitazar magnesium.

The details of one or more embodiments of the invention are set forth in the accompanying description.

BRIEF DESCRIPTION OF THE DRAWINGS

FIG. 1 discloses the X-ray diffractogram (XRD) of substantially pure saroglitazar magnesium as per example-1.

DETAILED DESCRIPTION OF THE INVENTION

The above and other objects of the present invention are achieved by the process of the present invention, which leads to saroglitazar magnesium and compositions thereof suitable for pharmaceutical use. The invention provides substantially pure saroglitazar magnesium suitable for development of finished formulations, which exhibit better control of impurities and stability under various stress conditions.

Optionally, the solution, prior to any solids formation, can be filtered to remove any undissolved solids, solid impurities prior to removal of the solvent. Any filtration system and filtration techniques known in the art can be used.

All ranges recited herein include the endpoints, including those that recite a range "between" two values. Terms such as "about", "generally", "substantially," and the like are to be construed as modifying a term or value such that it is not an absolute. This includes, at very least, the degree of expected experimental error, technique error and instrument error for a given technique used to measure a value.

The term "substantially pure" herein means saroglitazar magnesium has a purity of greater than or equal to 99% by weight, and dimer compound of Formula (IV) present in an amount relative to saroglitazar magnesium less than about 0.3% or sulfoxide compound of Formula (V) present in an amount relative to saroglitazar magnesium less than about 0.2% by area percentage of HPLC relative to saroglitazar magnesium. In particular, the saroglitazar magnesium comprises of one or more impurities within the permissible ICH limits suitable for pharmaceutical preparations. For example, but not limited to less than 0.15%, particularly less than 0.1% or more particularly less than 0.05% when measured by area percentage of HPLC relative to saroglitazar magnesium.

As used herein, the term "solution" or "reaction mixture" does not limit to a clear solution only and includes any hazy or opaque mass obtained.

As used herein, the term "obtaining" means isolating the saroglitazar magnesium by way of filtration, filtration under vacuum, centrifugation, decantation. The product obtained may be further or additionally dried to achieve the desired moisture values. For example, the product may be dried in a tray drier, dried under vacuum and/or in a Fluid Bed Drier.

The term "composition" used herein means a physical mixture of two or more components.

As used herein, the term "mean particle size" (also used interchangeably with "VMD" for "volume mean diameter") equal to or greater than a given diameter or being within a given particle size range means that the average of all saroglitazar magnesium particles in the sample have an estimated volume, based on an assumption of spherical shape, greater than or equal to the volume calculated for a spherical particle with a diameter equal to the given diameter as determined by laser diffraction in Malvern Master Sizer 2000 equipment or its equivalent.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The terms herein below are interchangeable and used in the description.
"DMF" refers to N,N-dimethylforamide.
"DMAc" refers to N,N-dimethylacetamide.
"DMSO" refers to N,N-dimethylsulfoxide.
"NMP" refers to N-methylpyrrolidone.
"THF" refers to tetrahydrofuran.
"MTBE" refers to methyl tert-butyl ether.
"TEA" refers to triethylamine.
"TBA" refers to tert-butyl amine.
"DIPA" refers to diisopropyl amine.
"DIPEA" refers to diisopropyl ethylamine.
"DBU" refers to 1,8-diazabicyclo[5.4.0]undec-7-ene.
"DABCO" refers to 1,4-diazabicyclo[2.2.2]octane.
"DBN" refers to 1,5-Diazabicyclo[4.3.0]non-5-ene.
"SMBA" refers to S-(−)-α-methylbenzyl amine.
"RRT" refers to relative retention time.
"HPLC" refers to high performance liquid chromatography.

In one general aspect there is provided a composition comprising saroglitazar magnesium and a dimer compound of Formula (IV).

In general, the composition comprising saroglitazar magnesium wherein the saroglitazar magnesium has a purity of greater than or equal to 99% by weight, and dimer compound of Formula (IV) present in an amount relative to saroglitazar magnesium less than about 0.3% by weight by area percentage of HPLC.

In one embodiment, the dimer compound comprises the structure of Formula (IV),

In some embodiments, the saroglitazar magnesium comprises less than about 0.25% by weight, less than about 0.2% by weight, less than about 0.15% by weight or less than about 0.1% by weight of dimer compound of Formula (IV) relative to saroglitazar magnesium by area percentage of HPLC.

In some embodiments, the saroglitazar magnesium comprises less than about 0.15% by weight, less than about 0.1%

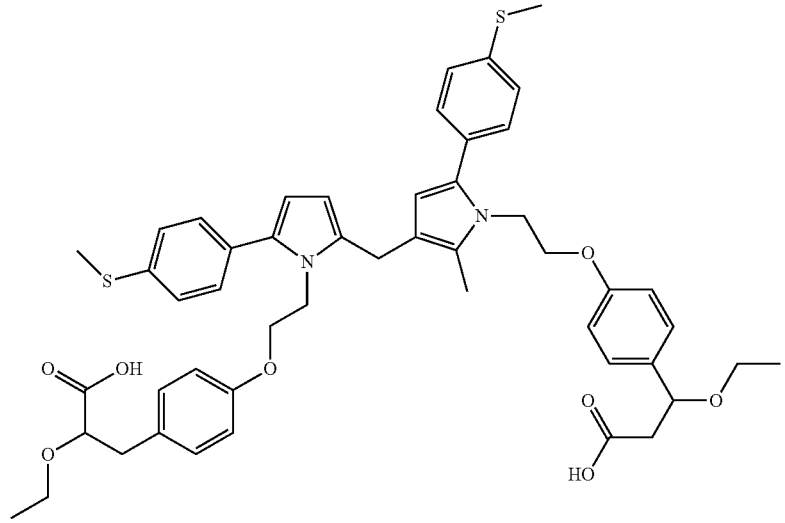 [SMILES: CCOC(Cc1ccc(OCCn2c(Cc3cc(-c4ccc(SC)cc4)n(CCOc4ccc(C(CC(=O)O)OCC)cc4)c3C)ccc2-c2ccc(SC)cc2)cc1)C(=O)O]

In another general aspect there is provided a composition of saroglitazar magnesium and a sulfoxide compound of Formula (V).

In general, the composition comprising saroglitazar magnesium wherein the saroglitazar magnesium has a purity of greater than or equal to 99% by weight, and sulfoxide compound of Formula (V) present in an amount relative to saroglitazar magnesium less than about 0.2% by weight by area percentage of HPLC.

In second embodiment, the sulfoxide compound comprises the structure of Formula (V),

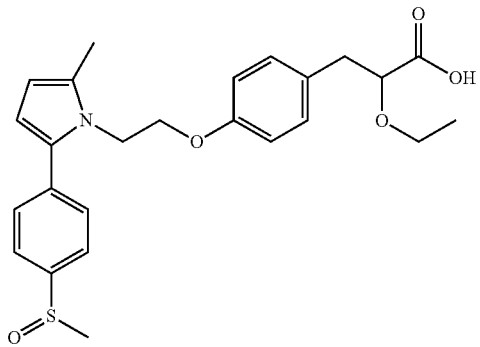

In another general aspect there is provided a composition comprising saroglitazar magnesium having a dimer compound (IV) present in an amount relative to saroglitazar magnesium less than about 0.3% or sulfoxide compound (V), present in an amount relative to saroglitazar magnesium less than about 0.2% by weight by area percentage of HPLC.

by weight, less than about 0.05% by weight of sulfoxide compound of Formula (V) relative to saroglitazar magnesium by area percentage of HPLC.

In general, the composition comprising saroglitazar magnesium wherein the saroglitazar magnesium has a purity of greater than or equal to 99% by weight, and impurities at RRT 1.06, RRT 1.27, RRT 1.41 and RRT 1.52 present in an amount relative to saroglitazar magnesium less than about 0.15% by weight by area percentage of HPLC.

In general, the composition comprising one or more of impurities at RRT 1.06, RRT 1.27, RRT 1.41 and RRT 1.52 in an amount relative to saroglitazar magnesium less than about 0.1% by weight by area percentage of HPLC.

In another general aspect, there is provided a dimer compound of Formula (IV).

In another general aspect, there is provided a sulfoxide compound of Formula (V).

In another general aspect there is provided a process for the preparation of substantially pure saroglitazar magnesium, the process comprising:

(a) reacting a hydroxy compound (A) with a mesylate compound (A1) in one or more solvents in the presence of a base to obtain an alkoxy ester compound of Formula (II),

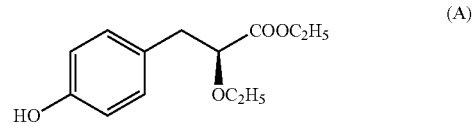

-continued

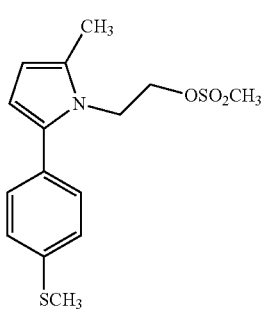

(A1)

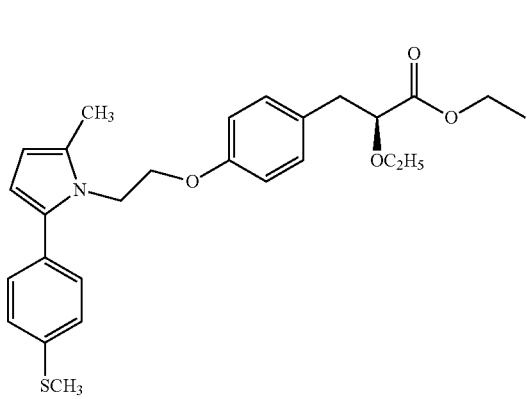

(II)

(b) hydrolyzing the alkoxy ester compound of Formula (II) with a base in one or more solvents at a lower temperature to obtain a reaction mixture;
(c) optionally, washing the reaction mixture with one or more solvents to obtain an aqueous layer;
(d) treating the aqueous layer with one or more solvents and adjusting the pH 2.0 to 6.0;
(e) extracting the aqueous layer with one or more solvents to obtain an organic layer;
(f) treating the organic layer with S-(−)-α-methylbenzyl amine to obtain saroglitazar S-(−)-α-Methyl benzyl amine (SMBA) salt of Formula (III);

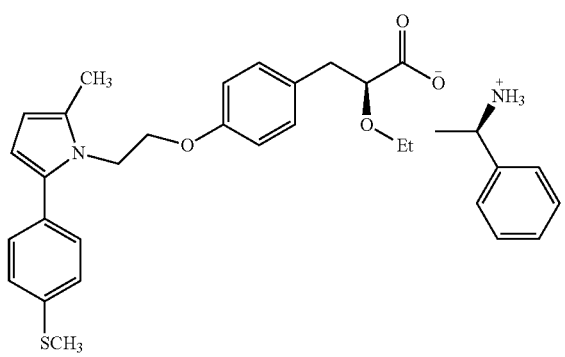

(III)

(g) purifying the saroglitazar SMBA salt with one or more solvents to obtain pure saroglitazar SMBA salt; and
(h) treating the pure saroglitazar SMBA salt with magnesium source to obtain substantially pure saroglitazar magnesium.

In general, the solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate; chlorinated hydrocarbons selected from methylene dichloride, ethylene dichloride, and chlorobenzene; hydrocarbons selected from pentane, hexane, heptane, and cyclohexane; ethers selected from tetrahydrofuran, 1,4-dioxane, diisopropyl ether, diethyl ether, and methyl tert-butyl ether; or mixture thereof. In particular, the mixture of cyclohexane and tetrahydrofuran may be used.

In general, the base comprises one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, potassium tert-butoxide, and sodium pentoxide. In particular, potassium carbonate is used. The base may be preferably anhydrous.

Optionally, the reaction may be catalyzed by a phase transfer catalyst. The phase transfer catalyst comprises one or more of tetrabutyl ammonium bromide (TBAB), tetrabutyl ammonium iodide (TBAI), benzyl triethyl ammonium chloride (TEBAC), polyethylene glycol (PEG-200, 400, 600, 800, 1000), crown ethers like 12-crown-4, 15-crown-5, 18-crown-6, dibenzo-18-crown-6, and diaza-18-crown-6. In particular, the phase transfer catalyst may be 18-crown-6.

In general, the reaction of a hydroxy compound (A) and a mesylate compound (A1) may be performed under heating at 35° C. to about reflux temperature of solvents. In particular, the reaction may be heated at 75° C. to 85° C. till the completion of the reaction. The reaction may be heated for about 35 hours to about 50 hours. Particularly for about 48 hours.

In another general aspect the obtained alkoxy ester (II) may be preceded further without isolating. Therefore, the alkoxy ester (II) may be further hydrolyzed in-situ.

The base for hydrolyzing the alkoxy ester (II) comprises one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, potassium tert-butoxide, and sodium pentoxide. In particular, sodium hydroxide may be used.

In general, the hydrolysis of the alkoxy ester at above room temperature results in increase of dimer impurity and sulfoxide compounds. Therefore, the hydrolysis of alkoxy ester is particular performed below 25° C., more particular from 18° C. to 22° C. to have reduced level of dimer compound and sulfoxide compound.

In general, the reaction mixture after hydrolysis of alkoxy ester compound of Formula (II) may be washed with one or more solvents. The solvent comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, methyl t-butyl ether, t-butyl acetate, n-butyl acetate, methylene dichloride, ethylene dichloride, and chlorobenzene, or mixture thereof. In particular, the mixture of water and methyl t-butyl ether may be used.

In general, the separated aqueous layer may be treated with one or more solvents and pH is adjusted 2.0 to 6.0 with hydrochloride acid solution. The pH is particular adjusted from about 5.0 to 6.0 and the organic layer is separated. In general, the solvent comprises one or more of methanol, ethanol, isopropanol, 2-propanol, 1-butanol, t-butyl alcohol, acetone, butanone, methyl isobutyl ketone, ethyl acetate, isopropyl acetate, isobutyl acetate, methyl t-butyl ether, t-butyl acetate, n-butyl acetate, methylene dichloride, ethylene dichloride, and chlorobenzene, or mixture thereof. In particular methyl t-butyl ether may be used.

The separated organic layer may be treated with S-(−)-α-methylbenzyl amine and stirred for 1-3 hours at 10° C.-35° C. to obtain saroglitazar SMBA salt. Particularly for about 2 hours at 20° C. Further, the reaction mass is filtered, washed with one or more solvent and dried to obtain to obtain saroglitazar S-(−)-α-methylbenzyl amine salt. The solvent comprises one or more of ethyl acetate, isopropyl acetate, isobutyl acetate, methyl t-butyl ether, t-butyl acetate, n-butyl acetate, methylene dichloride, ethylene dichloride, and chlorobenzene, or mixture thereof. In particular, methyl t-butyl ether may be used.

The saroglitazar SMBA salt may be purified with one or more solvents at 10° C.-30° C. to obtain pure saroglitazar SMBA salt. Particularly for about 2 hours at 20° C. The solvent comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, methyl t-butyl ether, t-butyl acetate, n-butyl acetate, methylene dichloride, ethylene dichloride, tetrahydrofuran and chlorobenzene, or mixture thereof. In particular mixture of tetrahydrofuran and water may be used.

The purification process mentioned above may be repeated to obtain pure saroglitazar SMBA salt.

In general, the pure saroglitazar SMBA salt Formula (III) may be treated with one or more solvents. The solvent comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, t-butyl acetate, n-butyl acetate, methylene dichloride, ethylene dichloride, and chlorobenzene, or mixture thereof. In particular, isopropyl acetate may be used.

The separated aqueous layer may be treated with a magnesium source to obtain saroglitazar magnesium. In general, the magnesium source comprises one or more of magnesium hydroxide, magnesium methoxide, magnesium acetate, magnesium chloride, and magnesium metal. In particular, the magnesium source may be magnesium acetate tetrahydrate in the form of its solution in water.

In general, the reaction mixture thus obtained may be extracted with one or more of solvents. The solvent comprises one or more of ethyl acetate, isopropyl acetate, isobutyl acetate, t-butyl acetate, n-butyl acetate, methylene dichloride, ethylene dichloride, and chlorobenzene, or mixture thereof. In particular, methylene dichloride may be used.

In general, the methylene dichloride may be removed by distillation under vacuum to obtain reaction mass, which is further treated with one or more solvents to obtain substantially pure saroglitazar magnesium. The solvent comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, t-butyl acetate, n-butyl acetate, methylene dichloride, ethylene dichloride, n-heptane and chlorobenzene, or mixture thereof. In particular, n-butyl acetate and n-heptane may be used.

In general, the substantially pure saroglitazar magnesium is amorphous characterized by x-ray powder diffraction pattern substantially as depicted in FIG. 1.

The product thus obtained may be dried under vacuum tray drier, sieved and milled to obtain suitable particle size range. The milled product may be further dried till constant weight is obtained to obtain the substantially pure saroglitazar magnesium.

In general, the product may be sieved through a 0.5 mm sieve followed by milling.

Examples of such milling include various makes of ball mills, roller mills, gyratory mills, multi-mills, and Jet-mills. Particularly mill such as Micros Super Fine Mill (available from Nara Machinery Co. Ltd or Tokyo, Japan), Multi-Mill Sr. No. G. 1.132 (available from Grooves International Pharmaceutical & Chemical Machinery), Jet-Mill from Midas Micronizer M-100 Aerosol (No. 154/07-08 (available from microtech Engineering Company) or a common mixer grinder can be used. Alternatively, other commercially available milling machine can be used.

In another general aspect there is provided substantially pure saroglitazar magnesium having a purity of at least about 99% by area percentage of HPLC. In particular, saroglitazar magnesium has a purity of at least about 99.5% by area percentage of HPLC.

In another general aspect there is provided substantially pure saroglitazar magnesium having a chiral purity of at least about 99% by area percentage of HPLC. In particular, saroglitazar magnesium having a chiral purity of at least about 99.5%, more particularly, a purity of at least about 99.9%, further more particularly, a purity of at least about 99.9% by area percentage of HPLC.

In another general aspect there is provided saroglitazar SMBA salt having a purity of at least about 99% by area percentage of HPLC. In particular, saroglitazar SMBA salt having a purity of at least about 99%, more particularly, a purity of at least about 99.5%, further more particularly, a purity of at least about 99.7%, by area percentage of HPLC.

In another general aspect there is provided a composition comprising saroglitazar SMBA salt wherein the saroglitazar SMBA salt has a purity of greater than or equal to 99% by weight, and dimer compound of Formula (IV) present in an amount relative to saroglitazar magnesium less than about 0.3% by weight by area percentage of HPLC.

In another general aspect there is provided a composition comprising saroglitazar SMBA salt wherein the saroglitazar SMBA salt has a purity of greater than or equal to 99% by weight, and sulfoxide compound of Formula (V) present in an amount relative to saroglitazar magnesium less than about 0.2% by weight by area percentage of HPLC.

In general, the composition comprising saroglitazar SMBA salt wherein the saroglitazar SMBA has a purity of greater than or equal to 99% by weight, and impurities at RRT 1.06, RRT 1.27, RRT 1.41 and RRT 1.52 present in an amount relative to saroglitazar SMBA less than about 0.1% by weight by area percentage of HPLC.

In general, the composition comprising saroglitazar SMBA salt wherein the saroglitazar SMBA has a purity of greater than or equal to 99% by weight, and impurities at RRT 1.06, RRT 1.27, RRT 1.41 and RRT 1.52 present in an amount relative to saroglitazar SMBA less than about 0.05% by weight by area percentage of HPLC.

TABLE 1

Summary of HPLC analysis of Saroglitazar SMBA salt

| Sample | Related substances by HPLC (%) | | | | | | |
|---|---|---|---|---|---|---|---|
| | HPLC Purity NLT 98.0% | Sulfoxide impurity NMT 0.5% | Dimer impurity NMT 0.5% | RRT 1.06 NMT 0.10% | RRT 1.27 NMT 0.10% | RRT 1.41 NMT 0.10% | RRT 1.52 NMT 0.10% |
| Saroglitazar SMBA salt before purification | 99.43 / 99.46 / 99.50 | 0.03 / 0.03 / 0.03 | 0.13 / 0.13 / 0.13 | 0.07 / 0.07 / 0.06 | 0.07 / 0.07 / 0.06 | 0.13 / 0.13 / 0.13 | 0.10 / 0.10 / 0.08 |
| Saroglitazar SMBA salt after first purification | 99.63 / 99.67 / 99.68 | 0.01 / 0.01 / 0.01 | 0.12 / 0.12 / 0.12 | 0.02 / 0.03 / 0.03 | 0.03 / 0.04 / 0.03 | 0.06 / 0.07 / 0.06 | 0.06 / 0.06 / 0.05 |
| Saroglitazar SMBA salt pure | 99.72 / 99.74 / 99.75 | ND / ND / ND | 0.11 / 0.12 / 0.11 | ND / ND / ND | 0.02 / 0.02 / 0.02 | 0.03 / 0.03 / 0.03 | 0.02 / 0.02 / 0.02 |

TABLE 2

Summary of HPLC analysis of Saroglitazar magnesium

| Sample | Related substances by HPLC (%) | | | | | | |
|---|---|---|---|---|---|---|---|
| | HPLC Purity NLT 98.0% | Sulfoxide impurity NMT 0.5% | Dimer impurity NMT 0.5% | RRT 1.06 NMT 0.10% | RRT 1.27 NMT 0.10% | RRT 1.41 NMT 0.10% | RRT 1.52 NMT 0.10% |
| Saroglitazar magnesium | 99.65 | 0.01 | 0.15 | 0.01 | 0.01 | 0.04 | 0.03 |

In another general aspect the unknown impurities at specific RRT are characterized by their m/z values. In particular the impurity at RRT 1.04 has m/z value of 875.3, RRT 1.25 has m/z value of 530.0, RRT 1.41 has m/z value of 640.2 and RRT 1.52 has m/z value of 438.2.

Powder X-ray Diffraction: X-ray powder diffraction spectrum was observed on a X-ray Powder diffractometer of make Rigaku or PANanalytical or equivalent make having a Copper Kα-radiation at a voltage of 40 kV and 30 mA. Approximately 150 mg sample was gently flattened on a quartz plate without further processing (e.g. Grinding and sieving) and scanned from 4° to 40° at 0.010° sampling width and 4.000° per minute.

In another general aspect there is provided a pharmaceutical composition comprising saroglitazar magnesium and dimer compound of Formula (IV) together with one or more pharmaceutically acceptable excipients, diluents and carriers.

In another general aspect there is provided a pharmaceutical composition comprising saroglitazar magnesium and sulfoxide compound of Formula (V) together with one or more pharmaceutically acceptable excipients, diluents and carriers.

In another general aspect, there is provided a pharmaceutical composition comprising substantially pure saroglitazar magnesium having a mean particle size equal to or less than 100 μm and one or more pharmaceutically acceptable excipients, diluents and carriers.

In general, the pharmaceutical compositions comprising saroglitazar magnesium of the invention may be prepared by using diluents or excipients such as fillers, bulking agents, binders, wetting agents, disintegrating agents, surface active agents, and lubricants.

Various modes of administration of the pharmaceutical compositions of the invention can be selected depending on the therapeutic purpose, for example tablets, pills, powders, liquids, suspensions, emulsions, granules, capsules, suppositories, or injection preparations.

In another general aspect substantially pure saroglitazar magnesium may be prepared by reaction scheme-1, which is also within the scope of the present invention.

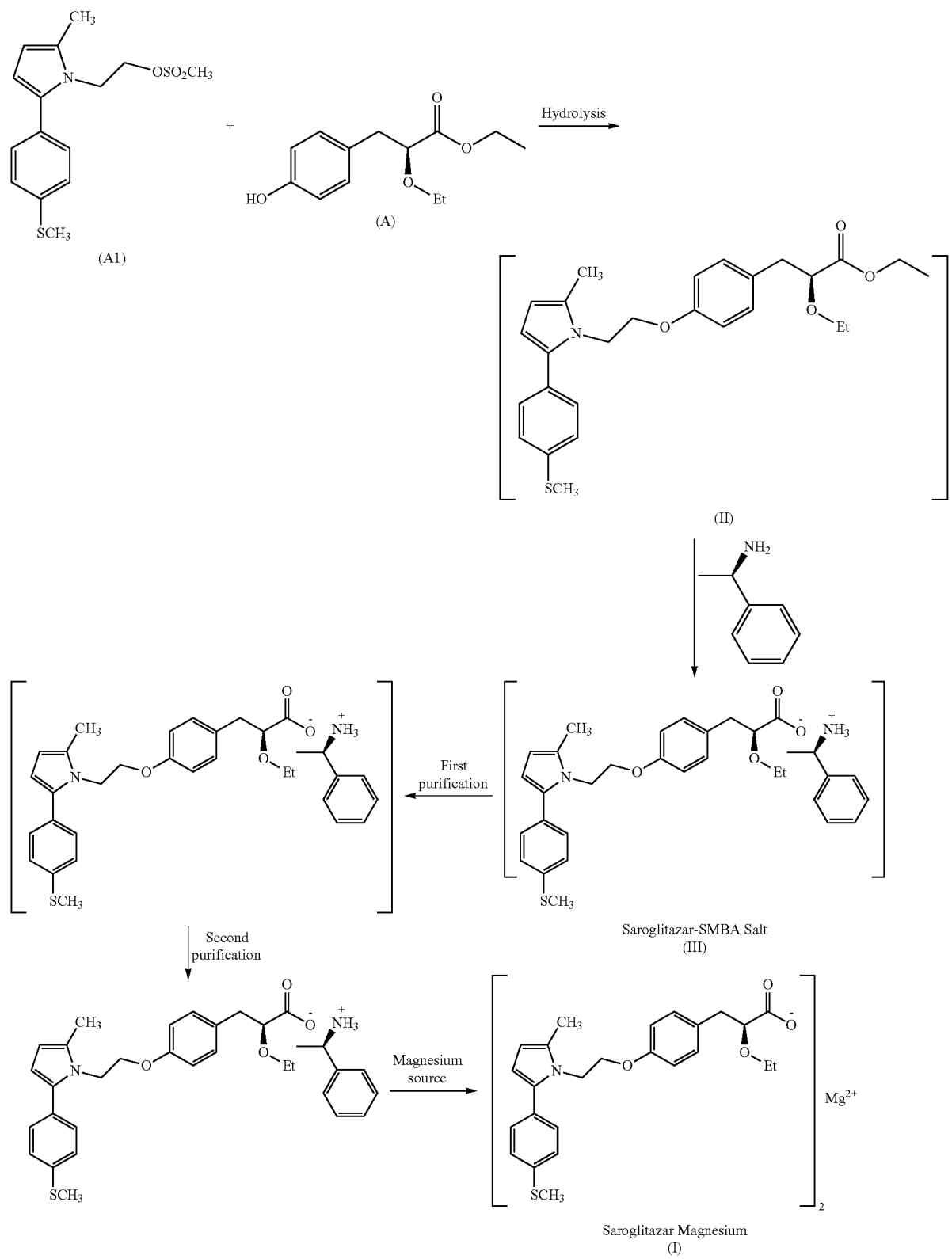

Scheme-1

Dosage

The effective amount of dose range of saroglitazar magnesium of Formula (I) of the present invention may be generally from 1 mg to 500 mg/day. The compound of Formula (I) may be administrated orally, intravenously, parentally or other forms of administration in the subject who is in need of treatment. Tablets, capsules, or other forms of presentation provided in discrete units may conveniently contain an amount of compound described herein which is effective at such dosage or as a multiple of the same, for instance, units containing 1 mg to 500 mg, in particular, 1 mg to 250 mg and more particularly 4 mg to 50 mg. The precise amount of compound prescribed to a patient will be the responsibility of the attendant physician. However, the dose employed will depend on a number of factors, including the age and sex of the patient, the precise disorder being treated, and its severity.

In another general aspect the saroglitazar magnesium and compositions described herein are useful for treatment of patient with a condition comprises one or more of prophylaxis of obesity, hyperlipidemia, hypercholesteremia, hypertension, atherosclerotic disease events, vascular restenosis, diabetes and to prevent or reduce the risk of developing atherosclerosis, which leads to diseases and conditions selected from arteriosclerotic cardiovascular diseases, stroke, coronary heart diseases, cerebrovascular diseases, peripheral vessel diseases and related disorders comprising administering the pharmaceutical compositions of the present invention.

The present invention is further illustrated by the following examples which are provided merely to be exemplary of the invention and do not limit the scope of the invention.

Certain modification and equivalents will be apparent to those skilled in the art and are intended to be included within the scope of the present invention.

EXAMPLES

Example-1

Preparation of Alkoxy Ester Compound

In a 5 Liter three necked round bottom flask equipped with nitrogen atmosphere facility, mechanical stirrer, thermometer and an addition funnel, 2-ethoxy-3-(4-hydroxyphenyl)-propionic acid ethyl ester (A) (100.0 g) and cyclohexane (1730.0 ml) were charged and reaction mixture was heated to 45° to 55° C. Potassium carbonate (58.0 g) was added and stirred for 30 min. methanesulfonic acid 2-[2-methyl-5-(4-methylsulfanyl-phenyl)-pyrrol-1-yl]-ethyl ester (A1) (150 g) and THF (265.0 ml) were added and heated to 75° C. to 85° C. for 48 hours. The reaction mixture was cooled to 25° to 35° C. and water (1000.0 ml) was added and stirred for 15 min. The separated aqueous layer was treated with cyclohexane (200.0 ml) and stirred for 15 min. The organic layers were combined and washed with caustic solution (600.0 ml). The separated organic layer was washed with water (600.0 ml) and characoalized with (5.0 g) charcoal and stirred for 30 min and filtered. The filtrate was distilled to remove cyclohexane and the residue was collected (residue-A).

Example-2

Preparation of Saroglitazar SMBA Salt:

In a 250 mL three necked round bottom flask equipped with nitrogen atmosphere facility, mechanical stirrer, thermometer and an addition funnel, residue-A obtained in example-1 and ethanol (400 mL) were stirred for 15 min. Sodium hydroxide 20.14 g solution in water (200.0 ml) was added and the reaction mixture was stirred for 3 hours at 18-22° C. MTBE (500 mL) was added into reaction mixture and stirred for 20 minutes. The reaction mixture was diluted with water (1800.0 ml) and stirred for 15 min. The separated aqueous layer was washed with MTBE (500 mL). The separated aqueous layer was diluted with MTBE (500 mL) and acidified with conc. HCl at adjust the pH 5-6. The separated aqueous layer was washed with MTBE. The combined organic layer was treated with (S)-(−)-methyl benzyl amine (61 g) and stirred for 1 hour at 25° C. and another one hour at 10-15° C. The reaction mixture was filtered and washed with MTBE. The wet-cake was dried to obtain crude saroglitazar SMBA salt.

Purification of Saroglitazar SMBA Salt

In a 1 Liter three mL three necked round bottom flask equipped with nitrogen atmosphere facility, mechanical stirrer, thermometer and an addition funnel, THF (125 mL) and saroglitazar SMBA salt (100 g) obtained in example-2 were added at 25° C. and stirred for 15 minutes. The reaction mixture was diluted with water (375 mL) stirred for 1 hour at 25° C. and another 1 hour at 10-15° C. The reaction mixture was filtered and washed with water. The wet-cake was dried to obtain pure saroglitazar SMBA salt. Repeat the second purification of saroglitazar SMBA salt using the same process mention above.

Example-3

Preparation of Saroglitazar Magnesium from Saroglitazar SMBA Salt:

In a 250 mL three necked round bottom flask equipped with nitrogen atmosphere facility, mechanical stirrer, thermometer and an addition funnel, saroglitazar SMBA obtained in example-2 (100 g) and isopropyl acetate (400 mL) were added at 25° C. The reaction mixture was diluted with water (250 ml) and acidified with conc. HCl at adjust the pH 2-3 and stirred for 15 minutes at 25° C. The organic layer was washed with brine solution and stirred for 15 min. The separated organic layer was treated with water and NaOH solution and stirred for 15 minutes at 25° C. The separated aqueous layer was treated with magnesium acetate tetrahydrate (38.3 g) in water (100 mL) solution and stirred for 60 min. The reaction mixture was extracted with methylene dichloride (400 mL). The separated organic layer was washed with brine solution and stirred for 15 minutes at 25° C. The separated lower organic layer was treated with magnesium sulfate. The mixture was filtered and washed with MDC. N-butyl acetate was added to filtrate then MDC was distilled out under vacuum below 40° C. The reaction mass was diluted with n-butyl acetate (30 ml). To the reaction mixture, n-heptane (900 mL) was added and stirred for 1 hour. The product was filtered and washed with n-heptane and dried in vacuum tray dryer at 25° C. to 35° C. for 3 hours. The product was sieved through 0.5 mm sieve and milled through jet-milled. The product was further dried in vacuum tray drier at 35° C. to 45° C. for 3 hours followed by drying at 55° C. to 65° C. at 12 hours to obtain amorphous saroglitazar magnesium (I). The compound is characterized by x-ray power diffraction (FIG. 1).

While the present invention has been described in terms of its specific embodiments, certain modifications and equivalents will be apparent to those skilled in the art and are intended to be included within the scope of the present invention.

We claim:

1. A composition comprising: saroglitazar magnesium wherein the saroglitazar magnesium has a purity of greater than or equal to 99% by weight; and a dimer compound of Formula (IV), wherein the dimer compound of Formula (IV) is present in the composition in an amount relative to saroglitazar magnesium of less than about 0.3% by weight by area percentage of HPLC.

2. The composition according to claim 1, wherein the dimer compound of Formula (IV) comprises the structure,

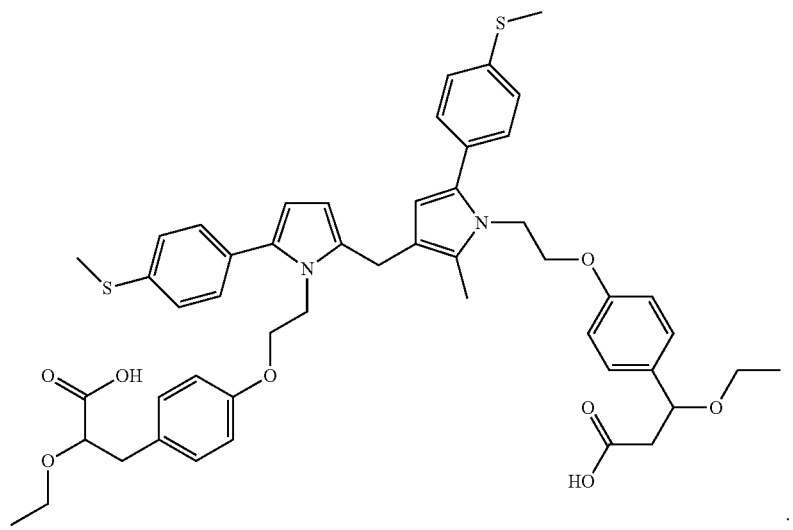 [SMILES: CCOC(Cc1ccc(OCCn2c(Cc3cc(-c4ccc(SC)cc4)n(CCOc4ccc(C(CC(=O)O)OCC)cc4)c3C)ccc2-c2ccc(SC)cc2)cc1)C(=O)O]

3. A composition comprising: saroglitazar magnesium wherein the saroglitazar magnesium has a purity of greater than or equal to 99% by weight; and a sulfoxide compound of Formula (V), wherein the sulfoxide compound of Formula (V) is present in the composition in an amount relative to saroglitazar magnesium of less than about 0.2% by weight by area percentage of HPLC.

4. The composition according to claim 3, wherein the sulfoxide compound of Formula (V) comprises the structure,

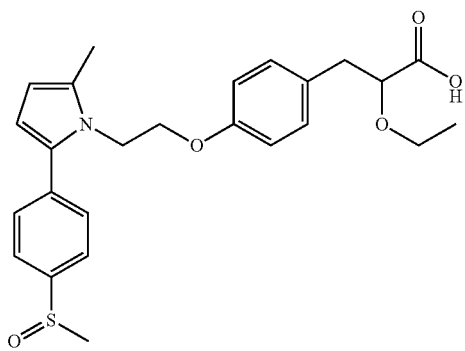

5. A dimer compound of Formula (IV),

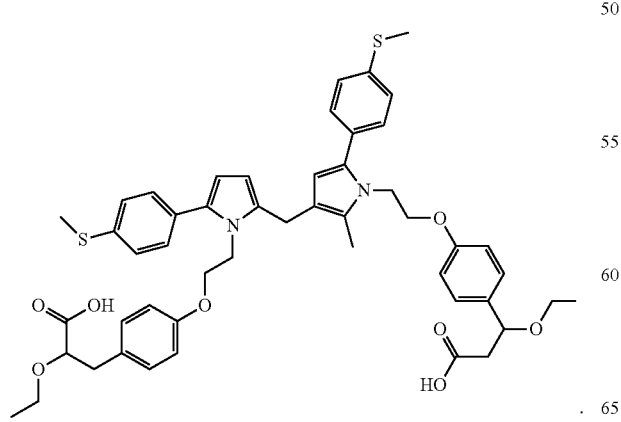

6. The composition according to claim 1, further comprising a sulfoxide compound of Formula (V), wherein the sulfoxide compound of Formula (V) is present in the composition in an amount relative to saroglitazar magnesium of less than about 0.2% by weight by area percentage of HPLC.

7. The composition according to claim 6, further comprising one or more impurities wherein the one or more impurities have a RRT at 1.06, 1.27, 1.41 and 1.52, wherein the one or more impurities is present in an amount relative to saroglitazar magnesium of less than about 0.15% by weight by area percentage of HPLC.

8. A pharmaceutical composition comprising saroglitazar magnesium according to claim 1.

9. A process for the preparation of a substantially pure saroglitazar magnesium, the process comprising:

(a) reacting a hydroxyl compound (A) with a mesylate compound (A1) in a mixture of solvents in the presence of a base to obtain an alkoxy ester compound of Formula (II),

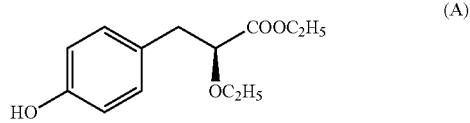

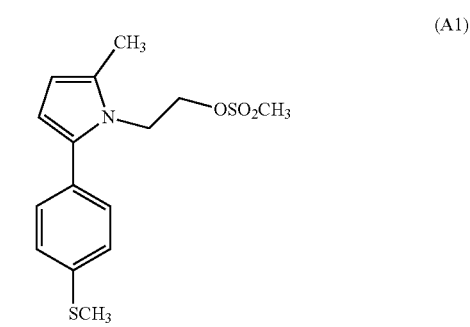

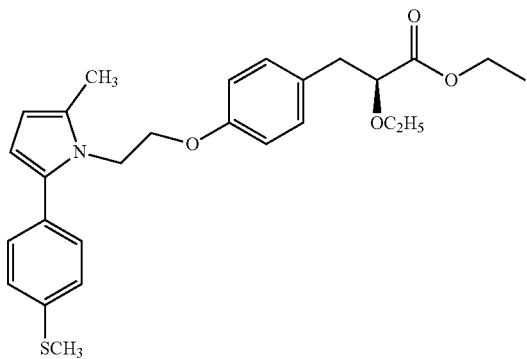

(b) hydrolyzing the alkoxy ester compound of Formula (II) with a base in one or more solvents at a lower temperature to obtain a reaction mixture;
(c) optionally, washing the reaction mixture with one or more solvents to obtain an aqueous layer;
(d) treating the aqueous layer with one or more solvents and adjusting the pH 2.0 to 6.0;
(e) extracting the aqueous layer with one or more solvents to obtain an organic layer;
(f) treating the organic layer with S-(−)-α-methylbenzyl amine to obtain a saroglitazar S-(−)-α-methylbenzyl amine (SMBA) salt of Formula (III);

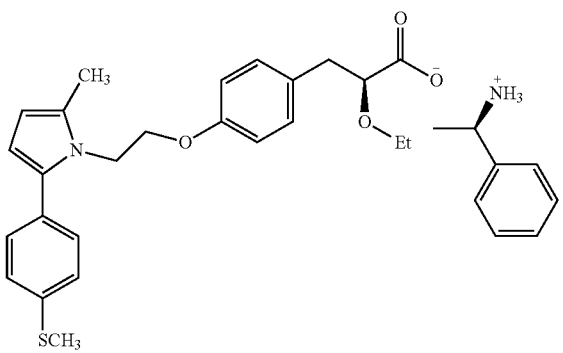

(g) purifying the saroglitazar SMBA salt with one or more solvents to obtain a pure saroglitazar SMBA salt; and
(h) treating the pure saroglitazar SMBA salt with a magnesium source to obtain the substantially pure saroglitazar magnesium.

10. The process according to claim 9, wherein the mixture of solvents in step (a) comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate; chlorinated hydrocarbons selected from methylene dichloride, ethylene dichloride, and chlorobenzene; hydrocarbons selected from pentane, hexane, heptane, and cyclohexane; ethers selected from tetrahydrofuran, 1,4-dioxane, diisopropyl ether, diethyl ether, and methyl tert-butyl ether; or a mixture thereof.

11. The process according to claim 9, wherein independently the base of step (a) and the base of step (b) comprise one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, potassium tert-butoxide, and sodium pentoxide.

12. The process according to claim 9, wherein the one or more solvents in step (c) comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, methyl t-butyl ether, t-butyl acetate, n-butyl acetate, methylene dichloride, ethylene dichloride, and chlorobenzene, or a mixture thereof.

13. The process according to claim 9, wherein the one or more solvents in step (g) comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, methyl t-butyl ether, t-butyl acetate, n-butyl acetate, methylene dichloride, ethylene dichloride, tetrahydrofuran and chlorobenzene, or a mixture thereof.

14. The process according to claim 9, wherein the magnesium source in step (f) comprises one or more of magnesium hydroxide, magnesium methoxide, magnesium acetate, magnesium chloride, and magnesium metal.

15. The process according to claim 9, wherein the substantially pure saroglitazar magnesium is an amorphous form, wherein the amorphous form is characterized by a x-ray powder diffraction pattern is substantially similar to that depicted in FIG. 1.

16. The process according to claim 9, wherein the saroglitazar SMBA salt of Formula (III) has a purity of greater than or equal to 99% by weight, and the dimer compound of Formula (IV) is present in an amount relative to saroglitazar magnesium of less than about 0.3% or the sulfoxide compound of Formula (V) is present in an amount relative to saroglitazar magnesium of less than about 0.2% by weight by area percentage of HPLC.

17. The process according to claim 9, wherein the saroglitazar SMBA salt has a purity of greater than or equal to 99% by weight, and wherein one or more impurities having a RRT at 1.06, 1.27, 1.41 and 1.52 are present in an amount relative to the saroglitazar SMBA salt of Formula (III) of less than about 0.1% by weight by area percentage of HPLC.

18. A pharmaceutical composition comprising: saroglitazar magnesium; a dimer compound of Formula (IV); and one or more pharmaceutically acceptable excipients, diluents and carriers.

19. A pharmaceutical composition comprising: saroglitazar magnesium; a sulfoxide compound of Formula (V); and one or more pharmaceutically acceptable excipients, diluents and carriers.

20. A method of treating a condition comprising administering the pharmaceutical composition according to claim 1, wherein the condition comprises one or more of prophylaxis of obesity, hyperlipidemia, hypercholesteremia, hypertension, atherosclerotic disease events, vascular restenosis, diabetes and to prevent or reduce the risk of developing atherosclerosis, which leads to diseases and conditions selected from arteriosclerotic cardiovascular diseases, stroke, coronary heart diseases, cerebrovascular diseases, peripheral vessel diseases and related disorders.

* * * * *

UNITED STATES PATENT AND TRADEMARK OFFICE
CERTIFICATE OF CORRECTION

| | | |
|---|---|---|
| PATENT NO. | : 10,385,017 B2 | Page 1 of 4 |
| APPLICATION NO. | : 15/748316 | |
| DATED | : August 20, 2019 | |
| INVENTOR(S) | : Sanjay Jagdish Desai et al. | |

It is certified that error appears in the above-identified patent and that said Letters Patent is hereby corrected as shown below:

In the Specification

At Column 3, Line number 10, delete the chemical structure:

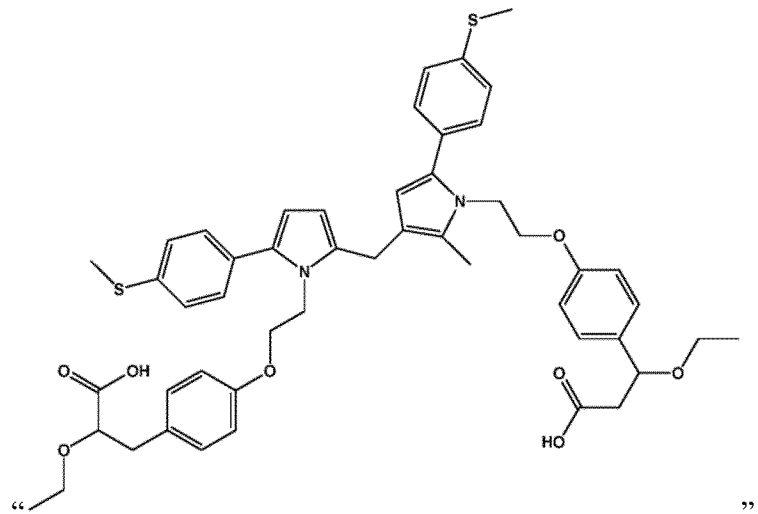

And insert therefor:

Signed and Sealed this
Twenty-seventh Day of June, 2023

*Katherine Kelly Vidal*

Katherine Kelly Vidal
*Director of the United States Patent and Trademark Office*

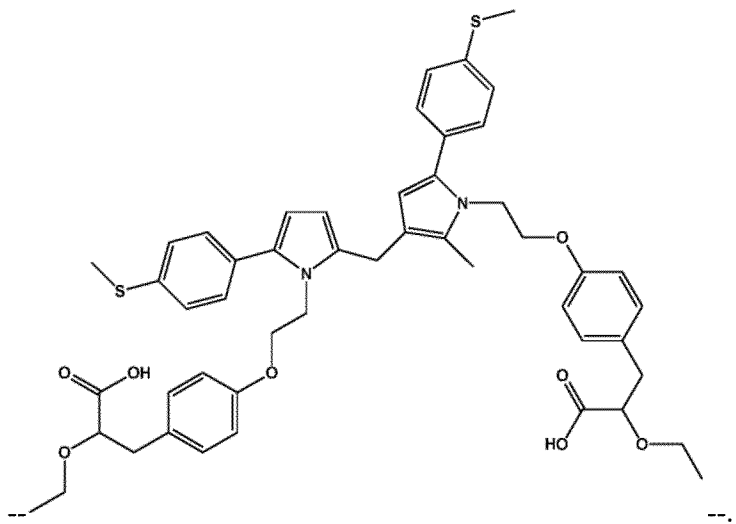
At Column 7, Line number 9, delete the chemical structure:
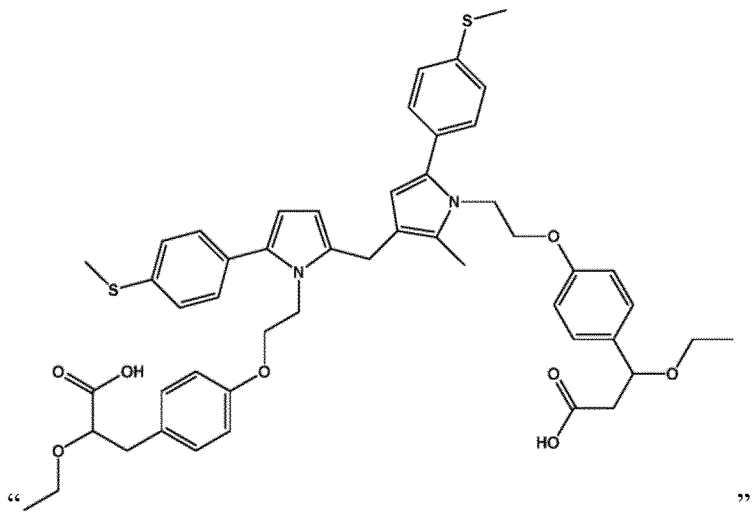
"                                                                "
And insert therefor:
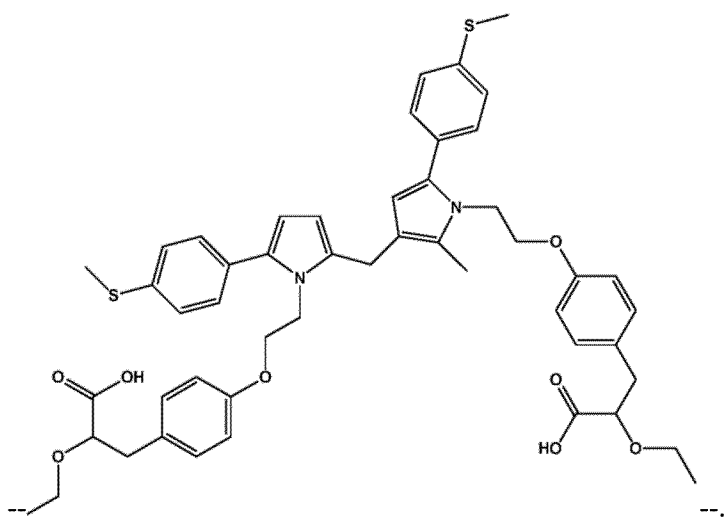

CERTIFICATE OF CORRECTION (continued)
U.S. Pat. No. 10,385,017 B2

In the Claims

At Column 19, Claim number 2, Line number 3, delete the chemical structure:

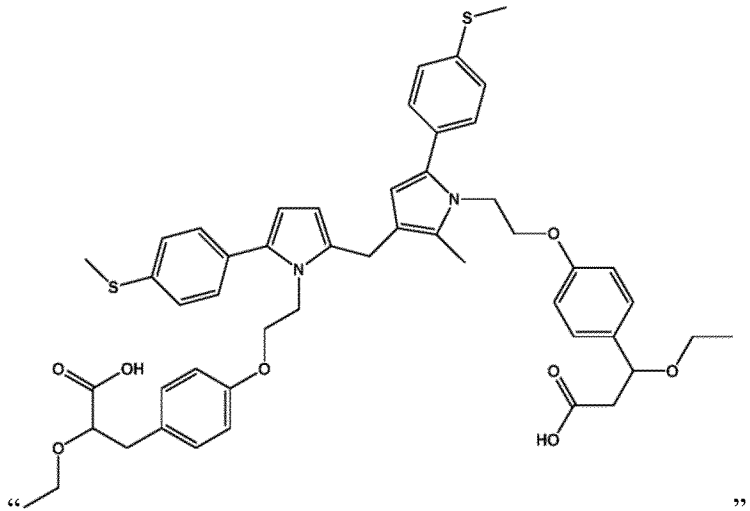

"

"

And insert therefor:

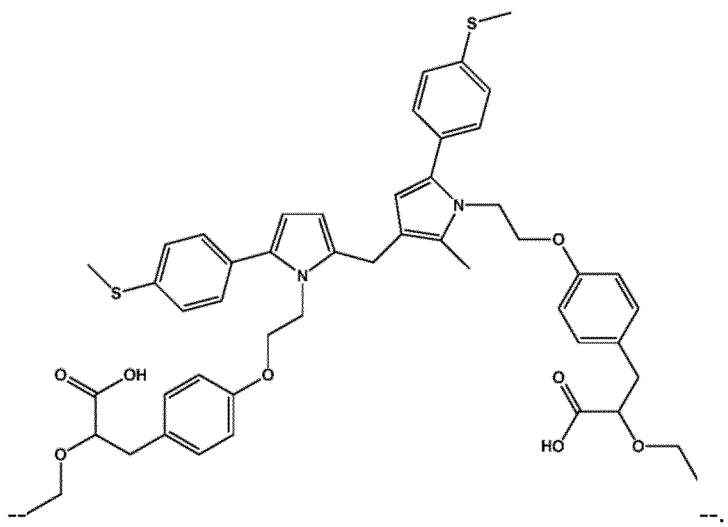

--.

CERTIFICATE OF CORRECTION (continued)
U.S. Pat. No. 10,385,017 B2

Page 4 of 4

At Column 19, Claim number 5, Line number 2, delete the chemical structure:

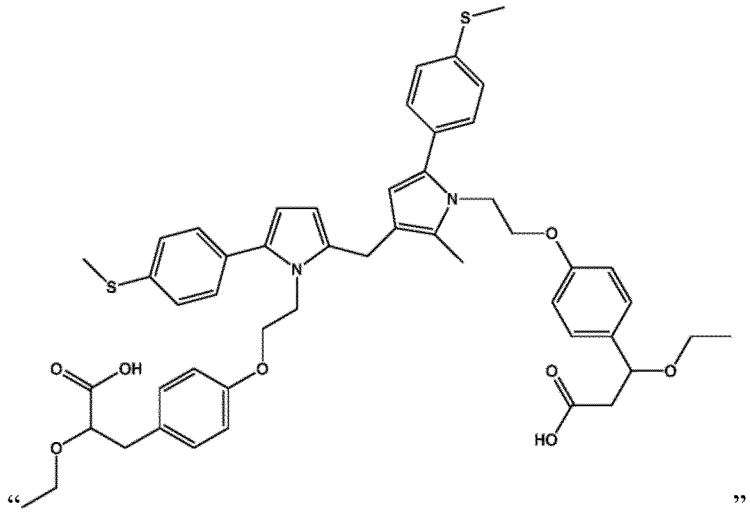

"        "

And insert therefor:

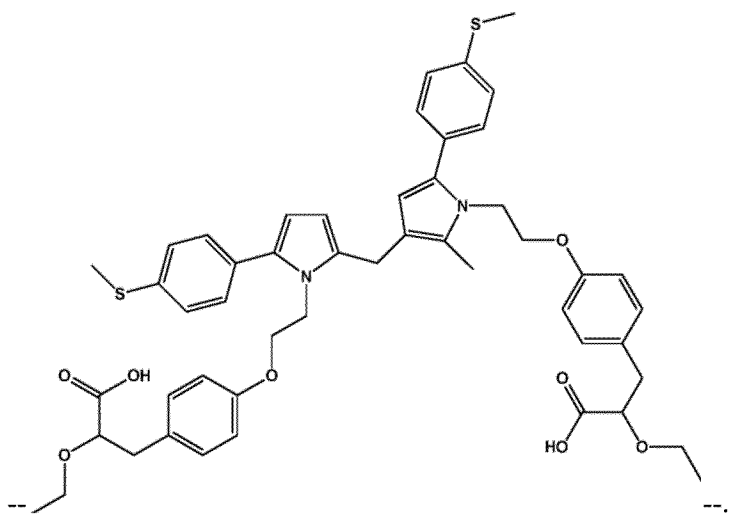

--        --.